United States Patent [19]

Houlihan et al.

[11] 4,015,010
[45] Mar. 29, 1977

[54] ALKANOYL SUBSTITUTED BENZOIC ACIDS AND ESTERS

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: Mar. 3, 1975

[21] Appl. No.: 554,508

[52] U.S. Cl. .................. 424/308; 260/473 R; 260/476 R; 260/515 R; 260/515 A; 424/317
[51] Int. Cl.² ............... A61K 31/235; A61K 31/19
[58] Field of Search ............ 424/308, 317; 260/515

[56] References Cited

UNITED STATES PATENTS

| | | | |
|---|---|---|---|
| 3,870,751 | 3/1975 | Haulihan et al. | 424/317 |
| 3,882,230 | 5/1975 | Holland | 424/317 |
| 3,907,878 | 9/1975 | Houlihan et al. | 424/308 |
| 3,919,309 | 11/1975 | Houlihan et al. | 424/317 |
| 3,924,003 | 12/1975 | Ho et al. | 424/331 |

*Primary Examiner*—Norman A. Drezin
*Attorney, Agent, or Firm*—Gerald D. Sharkin; Robert S. Honor; Timothy G. Rothwell

[57] ABSTRACT

Alkanoyl substituted benzoic acids and esters, e.g., p-pivaloyl ethyl benzoate, are prepared by oxidizing alkanoyl substituted toluene and reacting with lower alkanols and are useful as hypolipidemic, anti-obesity, and anti-diabetic agents.

25 Claims, No Drawings

ALKANOYL SUBSTITUTED BENZOIC ACIDS AND ESTERS

This invention relates to alkanoyl substituted benzoic acids and esters, which exhibit hypolipidemic, anti-obesity, and anti-diabetic activity. More particularly, it relates to p-pivaloyl benzoic acids and esters, and to processes for their preparation.

The compounds of this invention may be represented by the following structural formula:

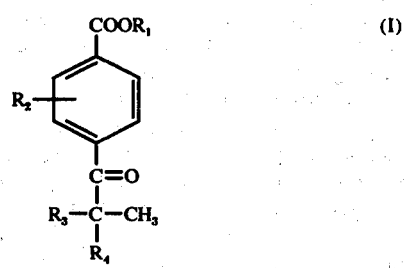

where $R_1$ represents hydrogen or straight chain lower alkyl, i.e., straight chain alkyl having 1 to 4 carbon atoms, e.g., methyl, ethyl, and the like, and $R_2$ represents hydrogen, halo having an atomic weight of about 19 to 36, i.e., fluoro or chloro, or straight chain lower alkoxy, i.e., straight chain alkoxy having 1 to 4 carbon atoms, e.g., methoxy, ethoxy, and the like, and $R_3$ and $R_4$ each independently represent lower alkyl having 1 to 2 carbon atoms, i.e., methyl or ethyl, provided that one of $R_1$ and $R_2$ is other than hydrogen.

The compounds of formula (I) in which $R_1$ represents straight chain lower alkyl may be prepared according to the following reaction scheme:

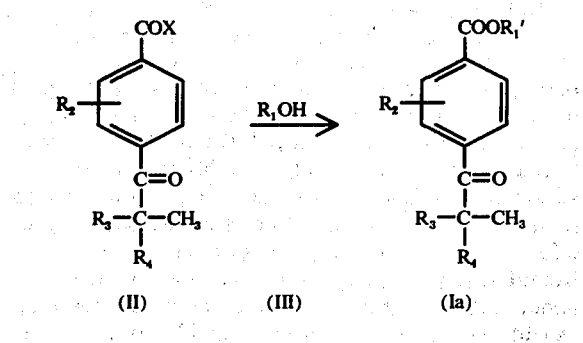

where

X is halo having an atomic weight of 35 to 80, or OH, $R_1'$ is straight chain lower alkyl as defined above, and where $R_2$, $R_3$, and $R_4$ are as defined above.

The compounds of formula (I) are prepared by reacting a compound of the formula (II) where X is a hydroxy group with a compound of the formula (III) in the presence of an acid and an inert organic solvent. Although the particular acid employed is not critical, it is preferred that the reaction be carried out in the presence of the mineral acids, e.g., hydrochloric acid, sulfuric acid, phosphoric acid, and the like, especially sulfuric acid. The particular solvent used is not critical, but it is preferred that the reaction be carried out in the presence of the inert organic solvents, such as acetone, dioxane, and the like, or an excess of the compound of formula (III) employed above, the latter being especially preferred. The temperature of the reaction is not critical, but it is preferred that the reaction be carried out at a temperature of from about 60° to 160° C., preferably the reflux temperature of the solvent. The reaction may be run from about 10 to 30 hours, preferably from about 16 to 20 hours. The resulting products are recovered using conventional techniques, e.g., evaporation followed by distillation.

The compounds of formula (I) in which $R_1$ represents hydrogen may be produced by the following reaction scheme:

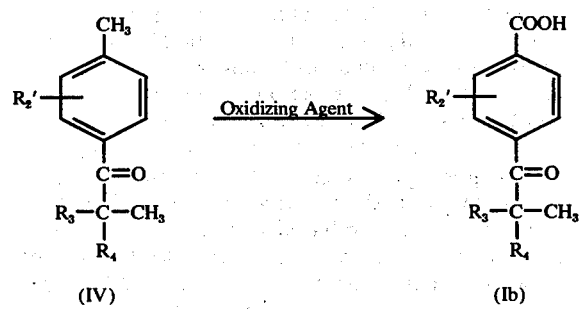

where $R_2'$ represents halo having an atomic weight of about 19 to 36, or straight chain lower alkoxy as defined above, and $R_3$ and $R_4$ are as defined above.

The compounds of formula (Ib) are prepared by treating a compound of the formula (IV) with an oxidizing agent such as potassium permanganate, potassium dichromate, and the like, preferably potassium permanganate, in the presence of a base and water as the aqueous organic solvent. Although the particular base employed is not critical, it is preferred that the reaction be carried out in the presence of an alkali metal hydroxide such as sodium hydroxide, potassium hydroxide, and the like, preferably potassium hydroxide. The particular solvent employed is critical, and the reaction must be run in the presence of water. The temperature of the reaction is not critical, but it is preferred that the process be carried out at a temperature between about 80° to 160° C., preferably the reflux temperature of the solvent. The reaction may be run from about 2 to 12 hours, preferably from about 4 to 6 hours. The product is recovered by conventional techniques, e.g., filtration followed by evaporation.

Another aspect of this invention converns the use of compounds of the following formula (Ic) as anti-obesity, anti-diabetic and hypolipidemic agents.

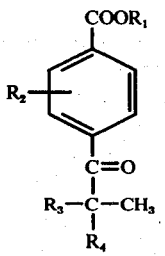

where $R_1$, $R_2$, $R_3$ and $R_4$ are as defined above, and the proviso is specifically excluded.

Many of the compounds of formula (II) in which X represents OH and $R_2$ represents hydrogen and formula (IV) are known and may be prepared by methods described in the literature. The compounds of formula (II) and (IV) not specifically described may be prepared from known starting materials by analogous methods.

The compounds of formula (Ic) are useful because they possess pharmacological activity in animals. In particular, the compounds of formula (Ic) are useful as anti-obesity agents in the treatment of obesity and anti-diabetic agents useful in the treatment of diabetes as indicated by (1) preventing an increase in the blood sugar level in male Wister rats in groups of four which have fasted for 16 hours and then are given an initial dose of 200 milligrams per kilogram of animal body weight of the test compound orally. One hour later, the rats are given 2 grams per kilogram of animal body weight of maltose load. Fifteen minutes after administration of the maltose, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxymethyl cellulose and are run concurrently, and by (2) preventing an increase in the blood sugar level in male Wistar rats in groups of four which are fasted for 16 hours and then are given an initial dose of 200 milligrams per kilogram of animal body weight of the test compound orally. One hour later, the rats are given 2.5 grams per kilogram of animal body weight of starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxymethyl cellulose and are run concurrently. The blood sugar levels are calculated and compared to the control.

The compounds of formula (Ic) are also useful as hypolipidemic agents, particularly as hypolipoproteinemic agents as indicated by the fall cholesterol and triglyceride levels in male albino Wistar rats weighing 110 to 130 g. initially. The rats are maintained on drug-free laboratory chow diet for seven days and then divided into groups of eight to 10 animals. Each group with the exception of the control is then given orally 30 to 250 milligrams per kilogram of body weight per diem of the compound for 6 days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, E., and Lederer, H., 1965, Technicon Symposium, Mediad, Inc., New York, 345–347), are added, and the mixture is shaken for 1 hour. Cholesterol and triglyceride levels are determined simultaneously on the same sample by Technicon N 24 A (cholesterol) and N 78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such uses, the compounds of formula (Ic) may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegent and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastrointestinal tract and thereby provide a sustained action over a longer period. Similarly, suspensions, syrups and elixirs may contain the active ingredient in admixture with any of the conventional excipients utilized by the preparation of such compositions, e.g., suspending agents such as methyl cellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier of adjuvant.

The anti-obesity effective dosage of active ingredient employed for the treatment of obesity and the anti-diabetic effective amount of active ingredient employed in the treatment of diabetes may vary depending on the particular compound employed, the mode of administration and the severity of the condition being treated. However, in general, satisfactory results are obtained for both the anti-obesity effect and the anti-diabetic effect when the compounds of formula (Ic) are administered at a daily dosage of from about 1 milligram to about 200 milligrams per kilogram of animal body weight, p.o., preferably given in divided doses two to four times a day, or in sustained release form. For most large mammals, the total daily dosage for both indications is from about 75 to about 1500 milligrams. Dosage forms suitable for internal use comprise from about 20 to about 750 milligrams of the active compound in intimate admixture with a solid or liquid pharmaceutically acceptable carrier or diluent.

The hypolipidemic effective dosage of compounds (Ic) employed in the alleviation of lipidemia may vary depending on the particular compound employed and the severity of the condition being treated. However, in general, satisfactory results are obtained when the compounds of formula (Ic) are administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 2500 milligrams. Dosage forms suitable for internal use comprise from about 75 to about 1250 milligrams of the active compound in intimate admixture with a solid or liquid pharmaceutically acceptable carrier or diluent.

A representative formulation suitable for oral administration is a tablet or capsule prepared by standard tabletting or encapsulating techniques which contains the following and may be administered 2 to 4 times a day in the treatment of obesity, diabetes or lipidemia.

| Ingredient | Weight (mg.) tablet | capsule |
|---|---|---|
| p-pivaloyl benzoic acid | 100 | 100 |
| tragacanth | 10 | — |
| lactose | 247.5 | 300 |
| corn starch | 25 | |
| talcum | 15 | |
| magnesium stearate | 2.5 | |
| Total | 400 mg. | 400 mg. |

EXAMPLE 1 o-fluoro-4-pivaloyl benzoic acid.

A mixture of 16.5 g. (0.085 mole) of 3'-fluoro-2,2,4'-trimethyl propiophenone, 30.0 g. (0.532 mole) potassium hydroxide and 150 ml. $H_2O$ is treated with 26.7 g. (0.170 mole) of potassium permanganate in 150 ml. of water. The resulting mixture is refluxed for 4 ½ hours. The cooled mixture is then treated with 5 ml. ethanol and filtered. The aqueous solution is extracted with ether and then acidified with concentrated hydrochloric acid. The resulting solid is washed with water and suspended in methylene chloride and then filtered. The methylene chloride filtrate is dried over anhydrous magnesium sulfate, filtered and evaporated in vacuo to give o-fluoro-4-pivaloyl benzoic acid.

Following the above procedure using in place of 3'-fluoro-2,2,4'-trimethyl propiophenone an equivalent amount of 3'-methoxy-2,2,4'-trimethyl propiophenone, there is obtained 4-pivaloyl-o-anisic acid.

EXAMPLE 2

4-pivaloyl ethyl benzoate.

A mixture of 20.6 g. (0.1 mole) of 4-pivaloyl benzoic acid, 150 ml. ethanol and 3 g. of concentrated sulfuric acid is refluxed for 18 hours. The resulting mixture is cooled and the excess alcohol removed in vacuo. The residue is dissolved in methylene chloride, washed with zinc sodium hydroxide, and then water. The methylene chloride is dried over anhydrous magnesium sulfate, filtered and evaporated in vacuo and the residue distilled to give 4-pivaloyl ethyl benzoate.

Following the above procedure and using in place of 4-pivaloyl benzoic acid an equivalent amount of
 a. o-fluoro-4-pivaloyl benzoic acid, or
 b. 4-pivaloyl-o-anisic acid,
there is obtained
 a. 2-fluoro-4-pivaloyl ethyl benzoate, or
 b. 2-methoxy-4-pivaloyl ethyl benzoate, respectively.

What is claimed is:
1. A method of treating obesity which comprises administering to a mammal in need of said treatment an anti-obesity effective amount of a compound of the formula:

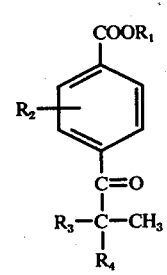

where
 $R_1$ represents hydrogen, or straight chain lower alkyl, and
 $R_2$ represents hydrogen, halo having an atomic weight of about 19 to 36, or straight chain lower alkoxy, and
 $R_3$ and $R_4$ each independently represent alkyl having 1 to 2 carbon atoms.

2. A method of treating diabetes which comprises administering to a mammal in need of said treatment an anti-diabetic effective amount of a compound of the formula:

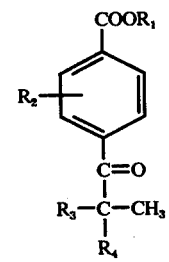

where
 $R_1$ represents hydrogen or straight chain lower alkyl, and
 $R_2$ represents hydrogen, halo having an atomic weight of about 19 to 36, or straight chain lower alkoxy, and
 $R_3$ and $R_4$ each independently represent alkyl having 1 to 3 carbon atoms.

3. A method of treating lipidemia which comprises administering to a mammal in need of said treatment a hypolipidemic effective amount of a compound of the formula:

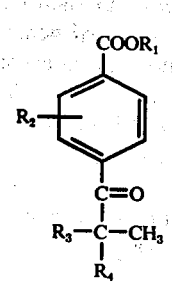

where
- $R_1$ represents hydrogen or straight chain lower alkyl, and
- $R_2$ represents hydrogen, halo having an atomic weight of about 19 to 36, or straight chain lower alkoxy, and
- $R_3$ and $R_4$ each independently represent alkyl having 1 to 2 carbon atoms.

4. The method of claim 1 in which the compound is:

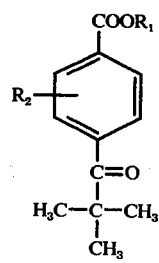

where $R_1$ and $R_2$ are as defined in claim 1.

5. The method of claim 2 in which the compound is:

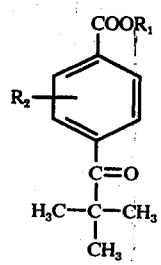

where $R_1$ and $R_2$ are as defined in claim 2.

6. The method of claim 3 in which the compound is:

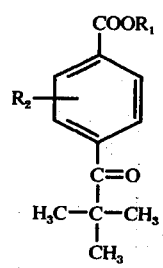

where $R_1$ and $R_2$ are as defined in claim 3.

7. The method of claim 1 in which the compound is:

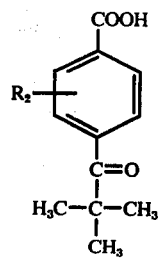

where $R_2$ is as defined in claim 1.

8. The method of claim 2 in which the compound is:

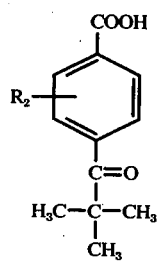

where $R_2$ is as defined in claim 2.

9. The method of claim 3 in which the compound is:

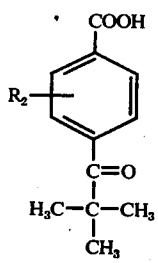

where $R_2$ is as defined in claim 3.

10. The method of claim 7 in which the compound is p-pivaloyl benzoic acid.

11. The method of claim 8 in which the compound is p-pivaloyl benzoic acid.

12. The method of claim 9 in which the compound is p-pivaloyl benzoic acid.

13. The method of claim 1 wherein the compound is administered orally at a daily dosage of from about 75 milligrams to about 1500 milligrams.

14. The method of claim 2 wherein the compound is administered orally at a daily dosage of from about 75 milligrams to about 1500 milligrams.

15. The method of claim 3 wherein the compound is administered orally at a daily dosage of from about 300 milligrams to about 2500 milligrams.

16. The method of claim 1 wherein the compound is orally administered in a unit dosage form comprising said compound to the extent of from about 20 milligrams to about 750 milligrams per unit dosage.

17. The method of claim 2 wherein the compound is orally administered in a unit dosage form comprising said compound to the extent of from about 20 milligrams to about 750 milligrams per unit dosage.

18. The method of claim 3 wherein the compound is orally administered in a unit dosage form comprising said compound to the extent of from about 75 milligrams to about 1250 milligrams per unit dosage.

19. A pharmaceutical composition useful as an anti-obesity, anti-diabetic and hypolipidemic agent comprising as an active ingredient thereof a compound of the formula:

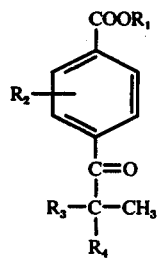

where
R₁, R₂, R₃, and R₄ are as defined in claim 1, and a pharmaceutically acceptable carrier therefor, said compound being present in said composition to the extent of from about 75 milligrams to about 1500 milligrams of said compound.

20. The composition of claim 19 in which the active ingredient is p-pivaloyl benzoic acid.

21. The composition of claim 20 in which the active ingredient is p-pivaloyl benzoic acid.

22. The composition of claim 21 in which the active ingredient is p-pivaloyl benzoic acid.

23. The pharmaceutical composition of claim 19 wherein said active ingredient is present in said composition to the extent of from about 20 milligrams to about 750 milligrams per unit dosage.

24. The pharmaceutical composition of claim 20 wherein said active ingredient is present in said composition to the extent of from about 20 milligrams to about 750 milligrams per unit dosage.

25. The pharmaceutical composition of claim 21 wherein said active ingredient is present in said composition to the extent of from about 75 milligrams to about 1250 milligrams per unit dosage.

* * * * *